United States Patent
Tammer

(10) Patent No.: US 12,215,074 B2
(45) Date of Patent: *Feb. 4, 2025

(54) PROCESS FOR THE PRODUCTION OF PEROXYESTERS

(71) Applicant: NOURYON CHEMICALS INTERNATIONAL B.V., Arnhem (NL)

(72) Inventor: Martinus Catharinus Tammer, Diepenveen (NL)

(73) Assignee: NOURYON CHEMICALS INTERNATIONAL B.V., Arnhem (NL)

(*) Notice: Subject to any disclaimer, the term of this patent is extended or adjusted under 35 U.S.C. 154(b) by 643 days.

This patent is subject to a terminal disclaimer.

(21) Appl. No.: 17/596,380

(22) PCT Filed: Jun. 11, 2020

(86) PCT No.: PCT/EP2020/066228
§ 371 (c)(1),
(2) Date: Dec. 9, 2021

(87) PCT Pub. No.: WO2020/249689
PCT Pub. Date: Dec. 17, 2020

(65) Prior Publication Data
US 2022/0235001 A1    Jul. 28, 2022

(30) Foreign Application Priority Data
Jun. 12, 2019  (EP) ..................... 19179621

(51) Int. Cl.
*C07C 407/00*  (2006.01)
*C07C 51/56*   (2006.01)

(52) U.S. Cl.
CPC ............ *C07C 407/00* (2013.01); *C07C 51/56* (2013.01)

(58) Field of Classification Search
CPC ..... C07C 407/00; C07C 409/38; C07C 51/56; C07C 53/124; Y02P 20/10
See application file for complete search history.

(56) References Cited

U.S. PATENT DOCUMENTS

| | | |
|---|---|---|
| 968,804 A | 8/1910 | Rigby |
| 1,001,155 A | 8/1911 | Litsey |
| 2,589,112 A | 3/1952 | Moise et al. |
| 3,079,443 A | 2/1963 | Barrett et al. |
| 3,138,627 A | 6/1964 | Harrison et al. |
| 3,264,346 A | 8/1966 | Weiberg |
| 3,397,245 A | 8/1968 | Appel et al. |
| 3,502,701 A | 3/1970 | Lewis et al. |
| 3,580,955 A | 5/1971 | Bafford |
| 3,595,898 A | 7/1971 | Harvey et al. |
| 3,956,396 A | 5/1976 | Mageli et al. |
| 4,002,539 A | 1/1977 | Strohmeyer et al. |
| 4,087,623 A | 5/1978 | Sherwin et al. |
| 4,613,463 A | 9/1986 | Sacks |
| 5,021,607 A | 6/1991 | Huybrechts |
| 5,281,571 A | 1/1994 | Woodard et al. |
| 5,654,463 A | 8/1997 | Abma et al. |
| 6,040,331 A | 3/2000 | Yamamoto et al. |
| 6,331,597 B1 | 12/2001 | Drumright et al. |
| 6,592,990 B2 | 7/2003 | Schwantes |
| 6,610,880 B1 | 8/2003 | Overkamp et al. |
| 6,803,420 B2 | 10/2004 | Cleary et al. |
| 7,049,467 B2 | 5/2006 | Paul et al. |
| 7,084,088 B2 | 8/2006 | Nishikido et al. |
| 7,112,314 B2 | 9/2006 | Brothers et al. |
| 7,253,312 B2 | 8/2007 | Bonnet et al. |
| 7,476,260 B2 | 1/2009 | Eliu et al. |
| 7,511,068 B2 | 3/2009 | Van Lommen et al. |
| 7,544,694 B2 | 6/2009 | Janssens et al. |
| 7,612,056 B2 | 11/2009 | Janssens et al. |
| 7,700,707 B2 | 4/2010 | Abhari et al. |
| 7,714,038 B2 | 5/2010 | Haering et al. |
| 7,799,093 B2 | 9/2010 | Brun et al. |
| 7,875,678 B2 | 1/2011 | Hanner et al. |
| 7,915,249 B2 | 3/2011 | Cid-Nunez et al. |
| 8,017,801 B2 * | 9/2011 | Appel ................. C07C 407/003 560/302 |
| 8,148,388 B2 | 4/2012 | Freyne et al. |
| 8,152,781 B2 | 4/2012 | Yang |
| 8,337,822 B2 | 12/2012 | Brun |
| 8,586,791 B2 | 11/2013 | Ansai et al. |
| 8,609,883 B2 | 12/2013 | Appel et al. |
| 8,663,459 B2 | 3/2014 | Al-Shahrani et al. |
| 8,680,299 B2 | 3/2014 | Scutt |
| 8,735,413 B2 | 5/2014 | Connolly et al. |
| 8,741,127 B2 | 6/2014 | Koseoglu et al. |
| 8,741,274 B2 | 6/2014 | Van et al. |
| 8,853,426 B2 | 10/2014 | Ishihara et al. |
| 9,017,648 B2 | 4/2015 | Barba et al. |
| 9,018,417 B2 | 4/2015 | Frey et al. |
| 9,090,548 B2 | 7/2015 | Cerd et al. |
| 9,119,879 B2 | 9/2015 | Du-Thumm et al. |
| 9,127,026 B2 | 9/2015 | Mariot et al. |
| 9,212,136 B2 | 12/2015 | Bader et al. |
| 9,221,028 B2 | 12/2015 | Dihora et al. |

(Continued)

FOREIGN PATENT DOCUMENTS

| | | |
|---|---|---|
| AU | 5310473 A | 9/1974 |
| CA | 488970 A | 12/1952 |
| CA | 1120055 A | 3/1982 |
| CA | 2167279 A1 | 2/1995 |
| CN | 1061777 A | 6/1992 |
| CN | 1151421 A | 6/1997 |
| CN | 1172105 A | 2/1998 |
| CN | 1342647 A | 4/2002 |
| CN | 1343247 A | 4/2002 |
| CN | 1368981 A | 9/2002 |

(Continued)

*Primary Examiner* — Yevgeny Valenrod
*Assistant Examiner* — Blaine G Doletski
(74) *Attorney, Agent, or Firm* — LORENZ & KOPF, LLP

(57) ABSTRACT

Process for the production of a peroxyester involving the reaction of an anhydride with an organic hydroperoxide, separation of the formed carboxylic acid, production of an anhydride from said carboxylic acid, and recycling of the anhydride within the process.

15 Claims, No Drawings

(56) References Cited

U.S. PATENT DOCUMENTS

| | | |
|---|---|---|
| 9,388,175 B2 | 7/2016 | Thuring et al. |
| 9,416,109 B2 | 8/2016 | Moniz et al. |
| 9,422,217 B2 | 8/2016 | Kon et al. |
| 9,649,264 B2 | 5/2017 | Ferrari et al. |
| 10,206,947 B2 | 2/2019 | Doxey et al. |
| 10,226,483 B2 | 3/2019 | Doxey et al. |
| 10,272,164 B2 | 4/2019 | Campbell et al. |
| 10,573,443 B2 | 2/2020 | Seidel et al. |
| 10,870,817 B2 | 12/2020 | Findlay et al. |
| 11,066,502 B2 | 7/2021 | Ulmer et al. |
| 11,266,584 B2 | 3/2022 | Tachon et al. |
| 2003/0004369 A1 | 1/2003 | Krasutsky et al. |
| 2005/0014974 A1 | 1/2005 | Paul et al. |
| 2005/0015974 A1 | 1/2005 | Frutschy et al. |
| 2005/0070664 A1 | 3/2005 | Takashima et al. |
| 2005/0119501 A1 | 6/2005 | Tammer et al. |
| 2005/0165600 A1 | 7/2005 | Kasravi et al. |
| 2007/0213346 A1 | 9/2007 | Janssens et al. |
| 2007/0224158 A1 | 9/2007 | Cassin et al. |
| 2008/0226581 A1 | 9/2008 | Luukas |
| 2009/0280069 A1 | 11/2009 | Godowski |
| 2010/0003205 A1 | 1/2010 | Elliott et al. |
| 2010/0003293 A1 | 1/2010 | Elliott et al. |
| 2010/0074928 A1 | 3/2010 | Elliott et al. |
| 2010/0031048 A1 | 12/2010 | Claudia |
| 2011/0136704 A1 | 6/2011 | Sharma et al. |
| 2011/0268778 A1 | 11/2011 | Dihora et al. |
| 2011/0269657 A1 | 11/2011 | Dihora et al. |
| 2012/0196988 A1 | 8/2012 | Gaboardi et al. |
| 2013/0142743 A1 | 6/2013 | Cavazzuti et al. |
| 2015/0099845 A1 | 4/2015 | Daga et al. |
| 2016/0213600 A1 | 7/2016 | Klostermann et al. |

FOREIGN PATENT DOCUMENTS

| | | |
|---|---|---|
| CN | 1100771 C | 2/2003 |
| CN | 1427771 A | 7/2003 |
| CN | 1463282 A | 12/2003 |
| CN | 1519649 A | 8/2004 |
| CN | 1537131 A | 10/2004 |
| CN | 1575204 A | 2/2005 |
| CN | 1660498 A | 8/2005 |
| CN | 1714068 A | 12/2005 |
| CN | 1720266 A | 1/2006 |
| CN | 1745069 A | 3/2006 |
| CN | 1847289 A | 10/2006 |
| CN | 1860197 A | 11/2006 |
| CN | 1933808 A | 3/2007 |
| CN | 1938291 A | 3/2007 |
| CN | 1942471 A | 4/2007 |
| CN | 1946723 A | 4/2007 |
| CN | 101107254 A | 1/2008 |
| CN | 101133091 A | 2/2008 |
| CN | 101249046 A | 8/2008 |
| CN | 101249047 A | 8/2008 |
| CN | 101263130 A | 9/2008 |
| CN | 100421646 C | 10/2008 |
| CN | 100540079 C | 9/2009 |
| CN | 101522177 A | 9/2009 |
| CN | 101522570 A | 9/2009 |
| CN | 1986635 B | 5/2010 |
| CN | 1911971 B | 11/2010 |
| CN | 101072779 B | 12/2010 |
| CN | 102076317 A | 5/2011 |
| CN | 102076318 A | 5/2011 |
| CN | 102076319 A | 5/2011 |
| CN | 102088956 A | 6/2011 |
| CN | 102092902 A | 6/2011 |
| CN | 102092904 A | 6/2011 |
| CN | 102092906 A | 6/2011 |
| CN | 102093909 A | 6/2011 |
| CN | 102131773 A | 7/2011 |
| CN | 102574933 A | 7/2012 |
| CN | 102666614 A | 9/2012 |
| CN | 102844054 A | 12/2012 |
| CN | 102858940 A | 1/2013 |
| CN | 1997340 B | 7/2013 |
| CN | 103228272 A | 7/2013 |
| CN | 103622842 A | 3/2014 |
| CN | 104093691 A | 10/2014 |
| CN | 104394835 A | 3/2015 |
| CN | 104672079 A | 6/2015 |
| CN | 103649278 B | 6/2016 |
| CN | 105705481 A | 6/2016 |
| CN | 105765672 A | 7/2016 |
| CN | 105793344 A | 7/2016 |
| CN | 105813617 A | 7/2016 |
| CN | 102858944 B | 8/2016 |
| CN | 104114524 B | 8/2016 |
| CN | 104114627 B | 9/2016 |
| CN | 105979969 A | 9/2016 |
| CN | 106029052 A | 10/2016 |
| CN | 103044645 B | 12/2016 |
| CN | 106278875 A | 1/2017 |
| CN | 102627778 B | 4/2017 |
| CN | 108423908 A | 8/2018 |
| CN | 109331871 A | 2/2019 |
| DE | 1518741 C2 | 6/1980 |
| EP | 0323663 A2 | 7/1989 |
| EP | 0616505 B1 | 9/1996 |
| EP | 0682695 B1 | 10/1997 |
| EP | 0639577 B1 | 5/2002 |
| EP | 1220837 B1 | 8/2004 |
| EP | 1445120 B1 | 7/2007 |
| EP | 1383824 B1 | 10/2008 |
| EP | 1372580 B1 | 9/2010 |
| EP | 2666763 A1 | 11/2013 |
| EP | 3047845 B1 | 6/2017 |
| FR | 2366059 A1 | 4/1978 |
| GB | 444603 A | 3/1936 |
| GB | 901041 A | 7/1962 |
| GB | 135372 A | 12/1968 |
| GB | 1156573 A | 7/1969 |
| JP | H01249752 A | 10/1989 |
| JP | H08245605 A | 9/1996 |
| JP | H08281077 A | 10/1996 |
| JP | 2003511440 A | 3/2003 |
| JP | 2004315536 A | 11/2004 |
| JP | 2006016393 A | 1/2006 |
| JP | 2007099624 A | 4/2007 |
| JP | 3921507 B2 | 5/2007 |
| JP | 4009007 B2 | 11/2007 |
| JP | 4317185 B2 | 8/2009 |
| JP | 2009542756 A | 12/2009 |
| JP | 2009542757 A | 12/2009 |
| JP | 2014064971 A | 4/2014 |
| JP | 2015523968 A | 8/2015 |
| KR | 1020140037915 A | 3/2014 |
| KR | 1020140099550 A | 8/2014 |
| KR | 1020150023843 A | 3/2015 |
| RU | 2286801 C2 | 11/2006 |
| RU | 2656332 C1 | 6/2018 |
| WO | 0046332 A1 | 8/2000 |
| WO | 02098924 A2 | 12/2002 |
| WO | 2010016493 A1 | 2/2010 |
| WO | 2020157061 A1 | 8/2020 |

\* cited by examiner

PROCESS FOR THE PRODUCTION OF PEROXYESTERS

CROSS-REFERENCE TO RELATED APPLICATION

This application is a U.S. National-Stage entry under 35 U.S.C. § 371 based on International Application No. PCT/EP2020/066228 filed Jun. 11, 2020 which was published under PCT Article 21(2) and which claims priority to European Application No. 19179621.8, filed Jun. 12, 2019, which are all hereby incorporated in their entirety by reference.

TECHNICAL FIELD

This present disclosure relates to a process for the preparation of peroxyesters.

BACKGROUND

Peroxyesters can be prepared by the reaction of an organic hydroperoxide and an acid anhydride or acid chloride with a base, as illustrated by the following equations:

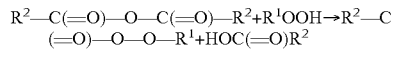

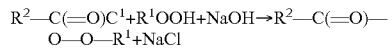

Acid chlorides are relatively expensive and generate chloride-containing water layers, which lead to waste waters with high salt concentration.

The anhydrides, on the other hand, are even more expensive than acid chlorides and the waste stream of this process contains a high organic load—i.e. a high Chemical Oxygen Demand (COD) value—due to the formed carboxylic acid salt, and is therefore economically and environmentally unattractive.

U.S. Pat. No. 3,138,627 discloses a process to prepare tertiary butyl peroxy esters by reacting an acid anhydride with a tertiary butyl hydroperoxide in a solvent and separating the formed peroxy ester from the reaction mixture by withdrawing the solvent therefrom such as by extraction, optionally followed by drying.

U.S. Pat. No. 6,610,880 discloses a process for the preparation of a peroxyester by reacting a mixed acid anhydride with an organic hydroperoxide, in which a peroxide and a carbonate monoester are formed. During work-up, the carbonate monoester decarboxylates to CO2 and an alcohol. Recycling of the alcohol requires phosgene. The mixed acid anhydride is prepared by contacting a carboxylic acid with a halogen formate. This route is most relevant for making peroxides where acid chlorides are expensive or not available, such as in the case of peroxides having a hydroxy group in the molecule.

BRIEF SUMMARY

This disclosure provides a process for the production of a peroxyester comprising the following steps:

a) producing a mixture comprising one or more peroxyesters and one or more carboxylic acid salts or adducts by reacting an anhydride with the formula $R^1$—C(=O)—O—C(=O)—$R^2$ with an organic hydroperoxide of the formula $R^3(OOH)_n$ in the presence of a base, wherein $R^1$ is chosen from linear and branched alkyl, cycloalkyl, aryl, and arylalkyl groups with about 1 to about 17 carbon atoms, optionally substituted with oxygen- and/or halogen-containing substituents, $R^2$ is chosen from linear and branched alkyl, cycloalkyl, aryl, and arylalkyl groups with about 2 to about 17 carbon atoms, optionally substituted with oxygen- and/or halogen-containing substituents, $R^3$ is a tertiary alkyl group with about 3 to about 18 carbon atoms, optionally substituted with oxygen- and/or halogen-containing groups and/or unsaturated groups, and n is an integer of from about 1 to about 3, b) separating the one or more carboxylic acid salts or adducts from the mixture produced in step a), c) liberating the carboxylic acid from the salt or adduct, d) optionally producing an additional amount of carboxylic acid by reacting an aldehyde of the formula $R^2$—C(=O)H with oxygen, e) reacting the carboxylic acid obtained in step c) and optionally an additional amount of carboxylic acid of the formula $R^2$—C(=O)OH—the additional amount of carboxylic acid being obtained from step d) and/or obtained in another way—with an acid anhydride or a ketene of the formula $C(R^4)_2$=C=O, each $R^4$ being independently chosen from H and $CH_3$, to form an anhydride with the formula $R^1$—C(=O)—O—C(=O)—$R^2$, and f) recycling at least part of the anhydride formed in step e) to step a).

DETAILED DESCRIPTION

The following detailed description is merely exemplary in nature and is not intended to limit the disclosure or the application and uses of the disclosure. Furthermore, there is no intention to be bound by any theory presented in the preceding background of the disclosure or the following detailed description.

It is an object of the present disclosure to provide a process for the production of peroxyesters—which term includes peroxydiesters, peroxytriesters, etc. and substituted peroxyesters such as hydroxyperoxyesters—that has an effluent with a relatively low COD value, which process does not require the use of acid chlorides and is economically and environmentally attractive.

This object can be achieved by a process comprising the following steps:

a) producing a mixture comprising one or more peroxyesters and one or more carboxylic acid salts or adducts by reacting an anhydride with the formula $R^1$—C(=O)—O—C(=O)—$R^2$ with an organic hydroperoxide of the formula R3(OOH)n in the presence of a base, wherein R1 is selected from linear and branched alkyl, cycloalkyl, aryl, and arylalkyl groups with about 1 to about 17 carbon atoms, optionally substituted with oxygen- and/or halogen-containing substituents, $R^2$ is selected from linear and branched alkyl, cycloalkyl, aryl, and arylalkyl groups with about 2 to about 17 carbon atoms, optionally substituted with oxygen- and/or halogen-containing substituents, $R^3$ is a tertiary alkyl group with about 3 to about 18 carbon atoms, optionally substituted with oxygen- and/or halogen-containing groups and/or unsaturated groups, and n is an integer in the range from about 1 to about 3, b) separating the one or more carboxylic acid salts or adducts from the mixture produced in step a), c) liberating the carboxylic acid from the salt or adduct, d) optionally producing an additional amount of carboxylic acid by reacting an aldehyde of the formula $R^2$—C(=O)H with oxygen, e) reacting the carboxylic acid obtained in step c) and optionally an additional amount of carboxylic acid of the formula $R^2$—C(=O)OH—said additional amount of carboxylic acid being obtained from step d) and/or obtained in another way—with an acid anhydride or a ketene of the formula $C(R^4)_2$=C=O, each $R^4$ being independently selected from H and CH3, preferably with acetic acid, to form an anhydride with the formula $R^1$—C(=O)—O—C(=O)—$R_2$, and f) recycling at least part of the anhydride formed in step e) to step a).

This process produces a peroxyester from an anhydride, which anhydride is obtained at least partly from the carboxylic acid side product. The recycling of the carboxylic acid side product makes this process economically attractive and its effluents low in COD.

Preferably, any additional amount of carboxylic acid that is required to form the amount of anhydride that is needed in step a) is obtained by oxidation of the corresponding aldehyde. It is therefore preferred to produce an additional amount of carboxylic acid in step d) and react it in step e) with acetic anhydride or a ketene.

As this process does not involve the use of corrosive or volatile reactants, it increases production safety and allows production at the location in which the peroxyester is eventually used (e.g. a polymerization facility). Such on-site production allows peroxide production on demand, thereby minimizing storage capacities and the consequential safety measures.

Step a) involves the reaction of an organic hydroperoxide with an anhydride with the formula $R^1$—C(=O)—O—C(=O)—$R^2$ in the presence of a base.

$R^1$ in this formula is selected from linear and branched alkyl, cycloalkyl, aryl, and arylalkyl groups with about 1 to about 17 carbon atoms, optionally substituted with oxygen- and/or halogen-containing substituents. Examples of suitable substituents are alkoxy, chlorine, and ester substituents. The number of carbon atoms is preferably about 2 to about 11, even more preferably about 2 to about 8, and most preferably about 3 to about 6 carbon atoms. In a further preferred embodiment, $R^1$ is selected from linear or branched alkyl groups. Most preferably, $R^1$ is selected from the group consisting of n-propyl, isopropyl, isobutyl, n-butyl, and 2-butyl groups.

$R^2$ in this formula is selected from linear and branched alkyl, cycloalkyl, aryl, and arylalkyl groups with about 2 to about 17 carbon atoms, optionally substituted with oxygen- and/or halogen-containing substituents. Examples of suitable substituents are alkoxy, chlorine, and ester substituents. The number of carbon atoms is preferably about 2 to about 11, even more preferably about 2 to about 8, and most preferably about 3 to about 6 carbon atoms. In a further preferred embodiment, $R^2$ is selected from linear or branched alkyl groups. Most preferably, $R^2$ is selected from the group consisting of n-propyl, isopropyl, isobutyl, n-butyl, and 2-butyl groups.

The anhydride can be symmetrical, meaning $R^1$=$R^2$, or asymmetrical, meaning that the $R^1 \neq R^2$.

If the anhydride is symmetrical, the carboxylic acid that is formed in step a) and extracted in step b) will have the formula $R^2$—C(=O)OH. If the anhydride is asymmetrical, the carboxylic acid will be a mixture of $R^2$—C(=O)OH and $R^1$—C(=O)OH.

Suitable symmetrical anhydrides are propionic anhydride, n-butyric anhydride, isobutyric anhydride, pivalic anhydride, valeric anhydride, isovaleric anhydride, 2-methyl butyric anhydride, 2-methylpentanoic anhydride, 2-methylhexanoic anhydride, 2-methylheptanoic anhydride, 2-ethyl butyric anhydride, caproic anhydride, caprylic anhydride, isocaproic anhydride, n-heptanoic anhydride, nonanoic anhydride, isononanoic anhydride, 3,5,5-trimethylhexanoic anhydride, 2-propylheptanoic anhydride, decanoic anhydride, neodecanoic anhydride, undecanoic anhydride, neoheptanoic anhydride, lauric anhydride, tridecanoic anhydride, 2-ethyl hexanoic anhydride, myristic anhydride, palmitic anhydride, stearic anhydride, phenylacetic anhydride, cyclohexanecarboxylic anhydride, 3-methyl-cyclopentanecarboxylic anhydride, beta-methoxy propionic anhydride, methoxy acetic anhydride, ethoxy acetic anhydride, propoxy acetic anhydride, alpha-ethoxy butyric anhydride, benzoic anhydride, o-, m-, and p-toluic anhydride, 2,4,6-trimethylbenzoic anhydride, o-, m-, and p-chlorobenzoic anhydride, o-, m-, and p-bromobenzoic anhydride, o-, m-, and p-nitrobenzoic anhydride, o-, m-, and p-methoxybenzoic anhydride, and mixtures of two or more of the abovementioned anhydrides.

Examples of suitable mixtures of symmetrical anhydrides are the mixture of isobutyric anhydride and 2-methylbutyric anhydride, the mixture of isobutyric anhydride and 2-methylpentanoic anhydride, the mixture of 2-methylbutyric anhydride and isovaleric anhydride, and the mixture of 2-methylbutyric anhydride and valeric anhydride.

Asymmetrical anhydrides are usually available as a mixture of the asymmetrical and symmetrical anhydrides. This is because asymmetrical anhydrides are usually obtained by reacting a mixture of acids with, e.g., acetic anhydride. This leads to a mixture of anhydrides, including an asymmetrical and at least one symmetrical anhydride. Such mixtures of anhydrides can be used in the process of the present disclosure. Examples of suitable asymmetrical anhydrides are isobutyric-2-methylbutyric anhydride, which is preferably present as admixture with isobutyric anhydride and 2-methylbutyric anhydride; isobutyric-acetic anhydride, which is preferably present as admixture with isobutyric anhydride and acetic anhydride, isobutyric-acetic anhydride, which is preferably present as admixture with isobutyric anhydride; 2-methylbutyric-valeric anhydride which is preferably present as admixture with 2-methylbutyric anhydride and valeric anhydride; and butyric-valeric anhydride, which is preferably present as admixture with butyric anhydride and valeric anhydride.

More preferred anhydrides are n-butyric anhydride, isobutyric anhydride, n-valeric anhydride, isovaleric anhydride, 2-methylbutyric anhydride, 2-methylhexanoic anhydride 2-propylheptanoic anhydride, isononanoic anhydride, cyclohexanecarboxylic anhydride, 2-ethylhexanoic anhydride, caprylic anhydride, caproic anhydride, 2-propylheptanoic anhydride, and lauric anhydride. Even more preferred are n-butyric anhydride, isobutyric anhydride, n-valeric anhydride, isovaleric anhydride, and 2-methylbutyric anhydride. Most preferred is isobutyric anhydride.

The organic hydroperoxide has the formula $R^3(OOH)n$, wherein $R^3$ is a tertiary alkyl group with about 3 to about 18 carbon atoms, optionally substituted with oxygen- and/or halogen-containing groups and/or unsaturated groups, and n is an integer in the range from about 1 to about 3, more preferably about 1 or about 2, and most preferably about 1. A preferred oxygen-containing group is a hydroxy group. Examples of unsaturated groups are alkynylene groups and unsaturated rings such as cyclohexenylene and phenylene groups.

$R^3$ preferably represents a C3-C18 tertiary alkyl group, more preferably a C3-C16 tertiary alkyl group, even more preferably a C3-C8 tertiary alkyl group, which may optionally contain further branches and/or hydroxy groups.

Typical examples of hydroperoxides that can be used in the present process include tert-butyl hydroperoxide, 1,1-dimethylpropyl hydroperoxide (i.e. tert-amyl hydroperoxide), 1,1-dimethylbutyl hydroperoxide (i.e. tert-hexyl hydroperoxide), 1-methyl-1-ethylpropyl hydroperoxide, 1,1-diethylpropyl hydroperoxide, 1,1,2-trimethylpropyl hydroperoxide, cumyl hydroperoxide, 1,1-dimethyl-3-hydroxybutyl hydroperoxide (i.e. hexylene glycol hydroperoxide), 1,1-dimethyl-3-hydroxypropyl hydroperoxide, 1,1-dimethyl-3-(2-hydroxyethoxy)butyl hydroperoxide, 1,1-dimethyl-3-(2-hydroxy-1-propyloxy)butyl hydroperoxide, 1,1-dimethyl-3-(1-hydroxy-2-propyloxy)butyl hydroperoxide, 1,1-dimethylpropenyl hydroperoxide, m-isopropylcumyl hydroperoxide, p-isopropylcumyl hydroperoxide, m-isopropenylcumyl hydroperoxide, p-isopropenylcumyl hydroperoxide, m-diisopropylbenzene dihydroperoxide, p-diisopropylbenzene dihydroperoxide, and 1,1,3,3-tetramethylbutyl hydroperoxide.

The preferred hydroperoxides are tert-butyl hydroperoxide, tert-amyl hydroperoxide, tert-hexyl hydroperoxide, 1,1,3,3-tetramethylbutyl hydroperoxide, 1,1-dimethyl-3-hydroxybutyl hydroperoxide, and cumyl hydroperoxide.

Most preferred are tert-butyl hydroperoxide, tert-amyl hydroperoxide, and 1,1,3,3-tetramethylbutyl hydroperoxide.

The organic hydroperoxide can be used in pure form or in a solution in water or organic solvent. Suitable organic solvents are alkanes (e.g. isododecane, Spiridane® and Isopar® mineral oils), chloroalkanes, esters (e.g. ethyl acetate, methyl acetate, dimethyl phthalate, ethylene glycol dibenzoate, dibutyl maleate, cumene, di-isononyl-1,2-cyclohexanedicarboxylate (DINCH), dioctyl terephthalate, or 2,2,4-trimethylpentanediol diisobutyrate (TXIB), ethers, amides, and ketones.

In one embodiment, the organic hydroperoxide is added as a solution in water, most preferably from about 30 to about 80 wt % aqueous solution. Specific examples of such solutions are solutions of ≥about 70 wt % tert-butyl hydroperoxide in water and ≥about 85 wt % tert-amyl hydroperoxide in water.

Other suitable organic hydroperoxide solutions are formulations containing ≥about 82% 1,1,3,3-tetramethylbutyl hydroperoxide in admixture with by-products, and ≥about 80% cumyl hydroperoxide in cumene.

The reaction of anhydride with organic hydroperoxide is conducted in the presence of a base.

Examples of suitable bases are alkylated amines, 4-(dimethylamino)pyridine and the oxides, hydroxides, bicarbonates, carbonates, (hydro)phosphates, and carboxylates of magnesium, lithium, sodium, potassium, or calcium. Other suitable bases are solid materials with basic functions that are able to capture the carboxylic acid, thereby forming an adduct. Examples of such solid materials are basic ion exchange resins such as poly(styrene-co-vinylbenzylamine-co-divinylbenzene), N-{2-[bis(2-aminoethyl) amino] ethyl}aminomethyl-polystyrene, diethylamino methyl-polystyrene, dimethyl aminomethylated copolymers of styrene and divinylbenzene, polymer-bound morpholine, poly(4-vinylpyridine), zeolites or mesoporous silicas containing alkylamine groups like 3-aminopropylsilyl-functionalized SBA-15 silica, polymeric amines, and mixtures of one or more of these materials. The formed adduct can be removed from the reaction mixture by filtration.

The base may be added in amounts of from about 80 to about 200 mol % relative to anhydride, more preferably from about 90 to about 150 mol %, and most preferably from about 100 to about 150 mol %.

The reaction of step a) is preferably performed at a temperature in the range of from about −10 to about 110° C., more preferably in the range from about 0 to about 80° C., and most preferably in the range from about 0 to about 50° C.

The molar ratio organic hydroperoxide to anhydride is preferably in the range from about 0.8 to about 1.6, more preferably from about 0.9 to about 1.4, and most preferably from about 0.95 to about 1.2.

The reaction does not require the presence of a solvent. However, if the final product (i.e. the peroxyester) requires dilution in a solvent, a solvent can be pre-charged with the anhydride or dosed to the reaction mixture during or after the reaction. Suitable solvents are alkanes, chloroalkanes, esters, ethers, amides, and ketones. Preferred solvents are (mixtures of) alkanes, such as isododecane, Spirdane®, Isopar® mineral oils; esters like ethyl acetate, methyl acetate, ethylene glycol dibenzoate, dibutyl maleate, di-isononyl-1,2-cyclohexanedicarboxylate (DINCH), or 2,2,4-trimethylpentanediol diisobutyrate (TXIB); and phthalates, such as dimethyl phthalate or dioctyl terephthalate.

According to step b), the carboxylic acid salt or adduct is separated from the mixture obtained in step a).

Separation can be performed by filtration or gravity, using conventional separation equipment, such as a liquid/liquid separator, a centrifuge, a (pulsed and or packed) counter current column, (a combination of) mixer settlers, or a continuous (plate) separator.

If desired, a small amount of a reducing agent, such as sulfite and/or iodide, may be added in order to decompose any organic hydroperoxides.

Any residual peroxy compounds in the aqueous phase can be removed by washing the aqueous phase with a solvent and/or an anhydride, preferably the anhydride of formula $R^1—C(=O)—O—C(=O)—R^2$.

After removal of the carboxylic acid, the organic phase containing the peroxyester may be purified and/or dried. Purification can be performed by washing with water, optionally containing salts, base, or acid, by filtration over, e.g., carbon black or diatomaceous earth, and/by adding a reducing agent (e.g. a sulfite solution) in order to lower the hydroperoxide content. Drying can be performed by using a drying salt like $MgSO_4$ or $Na_2SO^4$ or by using an air or vacuum drying step. If the peroxyester is to be emulsified in water, a drying step can be dispensed with.

The treatment with the reducing agent is preferably performed at about 5 to about 40° C. and a pH in the range from about 4 to about 8.

In step c), the carboxylic acid is liberated by, for instance,
(i) acidifying the aqueous phase containing the carboxylic acid salt,
(ii) splitting the adduct (e.g. by heating or acidification) and physically separating (e.g. distilling) the carboxylic acid from the solid material with basic functions, or
(iii) splitting the salt via electrochemical membrane separation, e.g., bipolar membrane electrodialysis (BPM).

Preferred acids for acidifying and protonating the carboxylic acid are acids with a pKa below about 3, such as $H_2SO_4$, HCl, $NaHSO_4$, $KHSO_4$, and the like. Most preferably $H_2SO_4$ is used. If $H_2SO_4$ is used, it is preferably added as an about 90 to about 96 wt % solution.

Acidification is preferably performed to a pH below about 6, more preferably below about 4.5, and most preferably below about 3. The resulting pH is preferably not lower than about 1.

In addition to acid, also a small amount of a reducing agent, such as sulfite and/or iodide, may be added to the aqueous phase in order to decompose any peroxide residues. A thermal treatment (e.g. at from about 20 to about 80° C.) can be applied in order to decompose any peroxyester residues.

The organic layer containing the carboxylic acid is then separated from any aqueous, salt-containing layer. Separation can be performed by gravity, using conventional separation equipment, such as a liquid/liquid separator, a centrifuge, a (pulsed and or packed) counter current column, (a combination of) mixer settlers, or a continuous (plate) separator.

In some embodiments, the separation can be facilitated by salting out the organic liquid phase with a concentrated salt solution, e.g. from about 20 to about 30 wt % NaCl, $NaHSO_4$, $KHSO_4$, $Na_2SO_4$, or $K_2SO_4$ solution. The salt reduces the solubility of the carboxylic acid in the aqueous liquid phase. This extraction can be performed in any suitable device, such as a reactor, centrifuge, or mixer-settler.

Especially for lower molecular weight acids, like butyric, isobutyric, pentanoic, and methyl or ethyl-branched pentanoic acids, a residual amount of the acid will remain dissolved in the aqueous layer. This residual amount can be recovered by adsorption, (azeotropic) distillation, or extraction. Optionally, a salt (e.g. sodium sulfate) can be added to the aqueous layer in order to lower the solubility of the carboxylic acid.

In another embodiment, liberation of the carboxylic acid is achieved by electrochemical membrane separation. Examples of electrochemical membrane separation techniques are membrane electrolysis and bipolar membrane electrodialysis (BPM). BPM is the preferred electrochemical membrane separation method.

Electrochemical membrane separation leads to splitting of the metal carboxylate in carboxylic acid and metal hydroxide (e.g. NaOH or KOH) and separation of both species. It thus leads to (i) a carboxylic acid-containing mixture and (ii) a NaOH or KOH solution, separated by a membrane.

The NaOH or KOH solution can be re-used in the process of the present disclosure, for instance in step a).

Depending on the temperature, the salt concentration, and the solubility of the carboxylic acid in water, the carboxylic acid-containing mixture can be a biphasic mixture of two liquid phases or a homogeneous mixture. If a homogeneous mixture is formed under the electrochemical membrane separation conditions (generally from about 40 to about 50° C.), cooling of the mixture to temperatures below about 30° C. and/or the addition of salt will ensure that a biphasic mixture will be formed. The organic liquid layer of this biphasic carboxylic acid-containing mixture can then be separated from the aqueous layer by gravity or by using equipment like a centrifuge.

The carboxylic acid-containing organic phase is optionally purified to remove volatiles like hydroperoxides, alcohols, ketones, alkenes and water before it is used in step e). These volatiles can be removed by adsorption, distillation, or drying with salt, molecular sieves, etc. Distillation is the preferred way of purification. The distillation preferably involves two product collection stages, one to collect impurities like alcohols and another to collect the remaining water, optionally as an azeotrope with the carboxylic acid.

According to steps e) and f), the carboxylic acid is subsequently reacted with an acid anhydride or a ketene of the formula $C(R_4)_2=C=O$—each $R^4$ being independently selected from H and $CH_3$— preferably with acetic anhydride, to form an anhydride with the formula $R^1$—C(=O)—O—C(=O)—$R^2$, which is subsequently at least partly recycled to step a) and used again to produce the peroxyester.

The reaction of step e), in particular the reaction with acetic anhydride, is advantageously performed in a reactive distillation column that is fed in the middle sections with the carboxylic acid and the acetic anhydride. The product anhydride is drawn from the bottom of the column and the product acetic acid is collected from the top of the column. An alternative method is to produce the anhydride in a stirred reactor surmounted by a distillation column. This allows the acetic acid to be distilled when formed in order to shift the equilibrium. US 2005/014974 discloses a process to prepare isobutyric anhydride by reacting acetic anhydride with isobutyric acid and containing a step of distilling of the acetic acid as formed. The distillation column is preferably sufficiently efficient to get high purity acetic acid. The efficiency of the column is preferably at least 8 theoretical plates. High purity acetic acid can be sold and/or used for various purposes.

The reaction with the ketene of the formula $C(R^4)_2=C=O$ is preferably performed in a counter-current adsorption device, as disclosed in U.S. Pat. No. 2,589,112. The preferred ketene has the formula $CH_2=C=O$.

A catalyst may be used in step e), although it is preferred to perform the reaction in the absence of catalyst. Examples of suitable catalysts are oxides, hydroxides, bicarbonates, carbonates, and carboxylates of magnesium, lithium, sodium, potassium, or calcium.

The molar ratio of carboxylic acid to acetic anhydride is preferably in the range from about 0.5:1 to about 5:1, more preferably from about 1.5:1 to about 2.2:1, most preferably from about 1.8:1 to about 2.2:1. A slight excess of carboxylic acid relative to acetic anhydride might be used.

The reaction is preferably performed at a temperature of from about 70 to about 200° C., preferably from about 100 to about 170° C., most preferably from about 120 to about 160° C. The temperature can be maintained at the desired value by adjusting the pressure in the reactor. This pressure is preferably in the range from about 1 to about 100 kPa, more preferably from about 5 to about 70 kPa.

After completion of the reaction, any excess acetic anhydride that may have been formed can be distilled off in order to purify the anhydride of formula $R^1$—C(=O)—O—C(=O)—$R^2$.

This anhydride can then be used again in step a).

In a preferred embodiment, the carboxylic acid that is used in step e) is obtained from two or three sources. The first source of carboxylic acid is the carboxylic acid that is liberated in step c). The second source of carboxylic acid is obtained by oxidation of the corresponding aldehyde in accordance with step d), as described below. The third source is an additional amount of carboxylic acid obtained in any other way.

As oxygen source for step d), air is preferably used, although pure oxygen, oxygen-enriched air, or oxygen-lean air may also be applied. The oxygen source can be added to the reaction mixture by feeding it as a gas to the reactor, preferably using a sparger.

The reaction of step d) is preferably performed at a temperature in the range of from about 0 to about 70° C., more preferably in the range from about 10 to about 60° C., and most preferably in the range from about 20 to about 55° C.

Atmospheric pressure is preferably used; at lower pressure the aldehyde may evaporate, which is undesired.

A catalyst may optionally be used. Very good catalysts, which not only accelerate oxidation but also increase the yield of acid, are platinum black and ferric salts. Cerium, nickel, lead, copper and cobalt salts are also useful, particularly their carboxylic acid salts.

The catalyst may be added in amounts of from about 0 to about 20 mol % relative to aldehyde, more preferably from about 0 to about 5 mol %, and most preferably from about 0 to about 2 mol %.

Examples of peroxyesters for which this process is especially suitable are tert-butylperoxy 2-ethylhexanoate, tert-amylperoxy 2-ethylhexanoate, tert-hexylperoxy 2-ethylhexanoate, 1,1,3,3-tetramethyl butyl-1-peroxy 2-ethylhexanoate, 1,1,3,3-tetramethylbutyl 1-peroxyneodecanoate, tert-butylperoxy neodecanoate, tert-amylperoxy neodecanoate, tert-hexylperoxy neodecanoate, 1,1,3,3-tetramethylbutyl 1-peroxyneoheptanoate, tert-butylperoxy neoheptanoate, tert-amylperoxy neoheptanoate, tert-hexylperoxy neoheptanoate, 1,1,3,3-tetramethylbutyl 1-peroxyneononanoate, tert-butylperoxy neononanoate, tert-amylperoxy neononanoate, tert-hexylperoxy neononanoate, tert-butylperoxy pivalate, tert-amylperoxy pivalate, tert-hexylperoxy pivalate, 1,1,3,3-tetramethyl butyl-1-peroxy pivalate, tert-butylperoxy 3,3,5-trimethylhexanoate, tert-amylperoxy 3,3,5-trimethylhexanoate, tert-hexylperoxy 3,3,5-trimethylhexanoate, 1,1,3,3-tetramethyl butyl-1-peroxy 3,3,5-trimethylhexanoate, tert-butylperoxy isobutyrate, tert-amylperoxy isobutyrate, tert-hexylperoxy isobutyrate, 1,1,3,3-tetramethyl butyl-1-peroxy isobutyrate, tert-butylperoxy n-butyrate, tert-amylperoxy n-butyrate, tert-hexylperoxy n-butyrate, tert-butylperoxy isovalerate, tert-amylperoxy isovalerate, tert-hexylperoxy isovalerate, 1,1,3,3-tetramethyl butyl-1-peroxy isovalerate, tert-butylperoxy n-valerate, tert-amylperoxy n-valerate, tert-hexylperoxy n-valerate, 1,1,3,3-tetramethyl butyl-1-peroxy n-butyrate, 1,1,3,3-tetramethyl butyl 1-peroxy m-chlorobenzoate, tert-butylperoxy m-chlorobenzoate, tert-amylperoxy m-chlorobenzoate, tert-hexylperoxy m-chlorobenzoate, 1,1,3,3-tetramethyl butyl 1-peroxy o-methylbenzoate, tert-butylperoxy o-methylbenzoate, tert-amylperoxy o-methylbenzoate, tert-hexylperoxy o-methylbenzoate, 1,1,3,3-tetramethyl butyl 1-butylperoxy phenylacetate, tert-butylperoxy phenylacetate, tert-amylperoxy phenylacetate, tert-hexylperoxy phenylacetate, tert-butylperoxy 2-chloroacetate, tert-butylperoxy cyclododecyloxalate, tert-butylperoxy n-butyloxalate, tert-butylperoxy 2-methylbutyrate, tert-amylperoxy 2-methylburyrate, 1,1-dimethyl-3-hydroxy butyl-1-peroxy neodecanoate, 1,1-dimethyl-3-hydroxy butyl-1-peroxy pivalate, 1,1-dimethyl-3-hydroxy butyl-1-peroxy 2-ethylhexanoate, 1,1-dimethyl-3-hydroxy butyl-1-peroxy-3,3,5-trimethylhexanoate, and 1,1-dimethyl-3-hydroxy butyl-1-peroxy isobutyrate.

Preferred peroxyesters include tert-butylperoxy isobutyrate, tert-amylperoxy isobutyrate, 1,1,3,3-tetramethyl butyl-1-peroxy isobutyrate, tert-butylperoxy n-butyrate, tert-amylperoxy n-butyrate, 1,1,3,3-tetramethyl butyl-1-peroxy n-butyrate, tert-butylperoxy isovalerate, tert-amylperoxy isovalerate, 1,1,3,3-tetramethyl butyl-1-peroxy isovalerate, tert-butylperoxy-2-methylbutyrate, tert-amylperoxy-2-methylbutyrate, 1,1,3,3-tetramethyl butyl-1-peroxy-2-methylbutyrate, tert-butylperoxy n-valerate, tert-amylperoxy n-valerate, and 1,1,3,3-tetramethyl butyl-1-peroxy n-valerate.

The process as contemplated herein and individual steps thereof can be performed batch-wise or continuously. Steps that are preferably performed in continuous mode are reactive distillation to make the anhydride in step e) and isolation and purification of the carboxylic acid in step c).

Also combinations of batch and continuous operation can be used. Examples of combinations are:
  a batch reaction to the peroxyester in step a), followed by a batch separation and continuous purification of carboxylic acid and continuous reactive distillation towards the anhydride in step e),
  a continuous reaction to peroxyester and separation and purification of the carboxylic acid, followed by a batch mode distillation to the anhydride in step e), or
  a batch reaction to peroxyester and separation of the product, followed by a continuous mode purification of carboxylic acid and continuous reactive distillation to the anhydride in step e).

The peroxyester obtained by the process as contemplated herein can be used in, e.g., the polymerization of monomers and/or the modification of polymers, in the usual amounts and using conventional methods. Specific examples of applications include polymerization of ethylene, vinyl chloride, styrene and (meth)acrylates. The peroxyesters are suitable in curing acrylates, unsaturated polyesters and vinyl esters, and the crosslinking of elastomers, rubbers, and olefins.

Hydroxyperoxyesters are particularly suitable for use in (co)polymer modification reactions, e.g. the preparation of hydroxy-functionalized poly(meth)acrylates. Said acrylates may be used for example in high solids coating resins.

EXAMPLES

Example 1

To an empty reactor equipped with a thermometer and a turbine impeller were charged 42.3 g heptane and 94.7 g 82% tert-amyl hydroperoxide, at 10° C. While stirring sufficiently fast to keep the reactor contents mixed, 122.5 g isobutyric anhydride and 125 g NaOH-25 wt % were dosed in 45 minutes at 10-15° C. The mixing was prolonged for 80 minutes, during which 7.6 g NaOH-25 wt % were added to maintain the pH above 12.

The water layer was separated from the organic layer and the organic layer was subsequently treated with a sulfite solution to destroy residual hydroperoxide. The resulting product was subsequently washed with a bicarbonate solution and dried with $MgSO_4\cdot2.H_2O$.

The product contained 68.3 wt % tert-amyl peroxy isobutyrate. The tert-amyl peroxy isobutyrate yield was 91%.

The water layer was washed with heptane in order to remove any residual tert-amylperoxy isobutyrate. To the separated aqueous phase sodium sulfite was added in order to reduce any residual hydroperoxides. The aqueous phase was then treated with 96 wt % $H_2SO_4$ to lower the pH to 2.5. The layers were allowed to separate by gravity at 40° C. The organic layer consisted of wet isobutyric acid.

After azeotropic removal of water in a rotary evaporator (200 mbar, 80° C.), the isobutyric acid was mixed with isobutyric acid from another source (in this case, Sigma Aldrich) and mixed with acetic anhydride in a molar ratio isobutyric acid:acetic anhydride of 2:1.05 and heated to distill acetic acid (<400 mbar at 120° C.) and to obtain isobutyric anhydride as the residue. This anhydride was then recycled to the first step.

Example 2

To a 300 ml beaker equipped with a stirrer and a thermometer surrounded by an ice bath, 40.4 grams 1,1,3,3-tetramethylbutylhydroperoxide (90.5 wt %; 0.25 mol) and 12.84 g n-nonane were added. The mixture was stirred and the temperature was maintained at 20° C. while dosing 39.9 g (0.25 mol) isobutyric anhydride in 30 minutes and 45 g 25 wt % NaOH (0.28 mol) in 100 minutes.

After 15 minutes post reaction, 20 g water was added and the layers were allowed to separate by gravity. The organic layer was removed and treated with a sulphite solution to reduce hydroperoxide and washed with a bicarbonate solution. The product was dried with magnesium sulphate and filtered over a glass filter to obtain a product containing 69.5 wt % 1,1,3,3-tetramethylbutyl peroxyisobutyrate (FT-IR peaks at 1774 cm$^{-1}$ and 1072 cm$^{-1}$).

The water layer (88.6 grams) was extracted twice with 20 g n-nonane at 20° C. in order to remove peroxyesters and hydroperoxide. The extracted aqueous phase was treated with 15.8 g 96 wt % $H_2SO_4$ to lower the pH to 2.5. The layers were allowed to separate by gravity at 40° C. The organic layer consisted of 25.3 g wet isobutyric acid.

After azeotropic removal of water in a rotary evaporator (200 mbar, 80° C.), the isobutyric acid was mixed with isobutyric acid from another source (in this case, from Sigma Aldrich) and mixed with acetic anhydride in a molar ratio isobutyric acid:acetic anhydride of 2:1.05 and heated to distill acetic acid (<400 mbar at 120° C.) and to obtain isobutyric anhydride as the residue. This anhydride was then recycled to the first step.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for production of a peroxyester comprising the following steps:
    a) producing a mixture comprising one or more peroxyesters and one or more carboxylic acid salts or adducts by reacting an anhydride with the formula $R^1$—C(=O)—O—C(=O)—$R^2$ with an organic hydroperoxide of the formula $R^3(OOH)_n$ in the presence of a base, wherein $R^1$ is chosen from linear and branched alkyl, cycloalkyl, aryl, and arylalkyl groups with 1-17 carbon atoms, optionally substituted with oxygen- and/or halogen-containing substituents, $R^2$ is chosen from linear and branched alkyl, cycloalkyl, aryl, and arylalkyl groups with 2-17 carbon atoms, optionally substituted with oxygen- and/or halogen-containing substituents, $R^3$ is a tertiary alkyl group with 3-18 carbon atoms, optionally substituted with oxygen- and/or halogen-containing groups and/or unsaturated groups, and n is an integer of 1-3,
    b) separating the one or more carboxylic acid salts or adducts from the mixture produced in step a),
    c) liberating the carboxylic acid from the salt or adduct,
    d) optionally producing an additional amount of carboxylic acid by reacting an aldehyde of the formula $R^2$—C(=O)H with oxygen,
    e) reacting the carboxylic acid obtained in step c) and optionally an additional amount of carboxylic acid of the formula $R^2$—C(=O)OH—the additional amount of carboxylic acid being obtained from step d) and/or obtained in another way—with an acid anhydride or a ketene of the formula $C(R^4)_2$=C=O, each $R_4$ being independently chosen from H and $CH_3$, to form an anhydride with the formula $R^1$—C(=O)—O—C(=O)—$R^2$, and
    f) recycling at least part of the anhydride formed in step e) to step a).

2. The process according to claim 1 wherein the carboxylic acid is reacted in step e) with acetic anhydride.

3. The process according to claim 1 wherein an additional amount of carboxylic acid is produced in step d) and reacted in step e).

4. The process according to claim 1 wherein the carboxylic acid is liberated from its salt in step c) by acidification.

5. The process according to claim 1 wherein the carboxylic acid is liberated from its salt in step c) by electrochemical membrane separation.

6. The process according to claim 1 further comprising, during step e), acetic acid is produced from the reaction of the acid anhydride and the carboxylic acid obtained in step c) and the acetic acid is removed from the reaction mixture, wherein the acid anhydride is acetic anhydride.

7. The process according to claim 1 wherein step e) is performed in a reactive distillation column.

8. The process according to claim 1 wherein $R^3$ is a tertiary alkyl group, optionally substituted with a hydroxy group.

9. The process according to claim 1 wherein n is either 1 or 2.

10. The process according to claim 9 wherein the organic hydroperoxide is chosen from tert-butyl hydroperoxide, tert-amyl hydroperoxide, tert-hexyl hydroperoxide, 1,1,3,3-tetramethylbutyl hydroperoxide, 1,1-dimethyl-3-hydroxybutyl hydroperoxide, and cumyl hydroperoxide.

11. The process according to claim 1 wherein $R^1$ and $R^2$ are individually chosen from linear and branched alkyl groups with about 2-17 carbon atoms, optionally substituted with a alkoxy group.

12. The process according to claim 11 wherein the anhydride of the formula $R^1$—C(=O)—O—C(=O)—$R^2$ is chosen from n butyric anhydride, isobutyric anhydride, n-valeric anhydride, isovaleric anhydride, isobutyric anhydride, 2-methylbutyric anhydride, 2-methylhexanoic anhydride 2-propylheptanoic anhydride, isononanoic anhydride, cyclohexanecarboxylic anhydride, 2-ethylhexanoic anhydride, caproic anhydride, caprylic anhydride, and lauric anhydride.

13. The process according to claim 1 wherein the peroxyester is chosen from tert-butylperoxy isobutyrate, tert-amylperoxy isobutyrate, 1,1,3,3-tetramethyl butyl-1-peroxy isobutyrate, tert-butylperoxy n-butyrate, tert-amylperoxy n-butyrate, 1,1,3,3-tetramethyl butyl-1-peroxy n-butyrate, tert-butylperoxy isovalerate, tert-amylperoxy isovalerate, tert-butylperoxy-2-methylbutyrate, tert-amylperoxy 2-methylbutyrate, 1,1,3,3-tetramethyl butyl-1-peroxy isovalerate, tert-butylperoxy n-valerate, tert-amylperoxy n-valerate, and 1,1,3,3-tetramethyl butyl-1-peroxy n-valerate.

14. The process according to claim 2 wherein an additional amount of carboxylic acid is produced in step d) and reacted in step e).

15. The process according to claim 1 wherein the carboxylic acid is liberated from its salt in step c) by bipolar membrane electrodialysis (BPM).

* * * * *